US00PP32263P2

(12) United States Plant Patent
Hansen

(10) Patent No.: US PP32,263 P2
(45) Date of Patent: Sep. 29, 2020

(54) ***KNIPHOFIA* PLANT NAMED 'JOKER'S WILD'**

(50) Latin Name: ***Kniphofia* hybrid**
Varietal Denomination: Joker's Wild

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/873,021

(22) Filed: Jan. 15, 2020

(51) Int. Cl.
*A01H 5/02* (2018.01)

(52) U.S. Cl.
USPC ..... Plt./443

(58) Field of Classification Search
USPC ..... Plt./443
See application file for complete search history.

*Primary Examiner* — Annette H Para

(57) ABSTRACT

A new and distinct cultivar of ornamental Red Hot Poker, *Kniphofia* plant named 'Joker's Wild', with long, gracefully-arching, strap-like, keeled, glaucous, gray-green foliage and numerous scapes beginning in late summer. Habit is densely-growing, winter-hardy and tolerant of heat. Numerous scapes with dense flowers of bright deep orange buds that retain their color when flowers open. The new plant is useful for landscaping as a specimen, en masse, or as a long-lasting cut flower.

1 Drawing Sheet

Botanical classification: *Kniphofia* hybrid.
Variety denomination: 'Joker's Wild'.

STATEMENT REGARDING PRIOR DISCLOSURES UNDER 37 CFR 1.77(B)(6)

The first non-enabling disclosure of the claimed plant, in the form of a photograph and brief description, was made by Walters Gardens, Inc. on Feb. 1, 2019 on their website. Subsequently, on May 29, 2019, the claimed plant was displayed with a photograph and brief sales promotion on the "Walters Gardens 19-20 Catalog." Walters Gardens, Inc. sold the first plants of 'Joker's Wild' on Mar. 23, 2019. Walters Gardens, Inc. obtained the new plant and all information relating thereto, from the inventor. No plants of *Kniphofia* 'Joker's Wild' have been sold, in this country or anywhere in the world nor has any disclosure of the new plant been made more than one year prior the filing date of this application, and any such sale or disclosure of the new plant within one year was either derived directly or indirectly from the inventor.

BACKGROUND AND ORIGIN OF THE PLANT

The present invention relates to the new and distinct Red Hot Poker, *Kniphofia* 'Joker's Wild' developed under the direction of the inventor at a wholesale perennial nursery in Zeeland, Mich., USA in the summer of 2013. The new plant was the result of a single seedling selection from a self-pollination of 'Alcazar' (not patented) on Jul. 28, 2014. The plant passed initial evaluation in the summer of 2016 and was subsequently given the breeder code 14-9-1 prior to naming. *Kniphofia* 'Joker's Wild' has been successfully asexually propagated by division method since 2016 at the same wholesale perennial nursery in Zeeland, Mich. and subsequently by shoot tip tissue culture, and both methods have been found to be stable and produce identical plants that maintain the unique characteristics of the original plant through successive generations.

SUMMARY OF THE PLANT

*Kniphofia* 'Joker's Wild' differs from its parent as well as all other *Kniphofia* known to the applicant. The most similar known *Kniphofia* cultivars are: 'Backdraft' U.S. Plant Pat. No. 31,424, 'Ember Glow' U.S. Plant Pat. No. 23,000, 'Jackpot' U.S. Plant Pat. No. 31,283, 'High Roller' U.S. Plant patent application Ser. No. 16/350,857, 'Poker Face' U.S. Plant Pat. No. 31,346, 'Mango Popsicle' and 'Orange Blaze' U.S. Plant Pat. No. 31,545. 'Backdraft' is shorter in scape and foliage and the flower is reddish-orange opening to peachy-yellow, and the flowering season is slightly longer. 'Ember Glow' is about half the height and the flowers are a lighter orange opening to yellow and the flower heads are smaller. 'Jackpot' is shorter in habit and the flowers open to yellow with more flowers per stem. 'High Roller' is slightly shorter in habit and the flowers begin a deeper reddish orange and lighten to near white. 'Poker Face' is slightly shorter in habit and the flowers are a lighter orange. 'Mango Popsicle' is shorter in scape and foliage height, the flowers are lighter orange with fewer flowers per inflorescence. 'Orange Blaze' has a much shorter habit, the flowers are lighter orange and there are fewer flowers per stem. 'Alcazar' has buds that begin more reddish-orange then lighten to orange and open yellowish on significantly taller plants.

*Kniphofia* 'Joker's Wild' differs from these above cultivars and all cultivars known to the inventor in that it has:

1. Gracefully arching, strap-like, keeled, gray-green foliage.
2. Rapidly growing, dense habit, winter-hardy, heat tolerant, rabbit and deer tolerant, moderate-sized clumps.
3. Numerous spikes of bright deep orange buds on medium height stems that retain their color when open on medium height stems;

4. Flowering beginning late summer for three weeks in Michigan.

BRIEF DESCRIPTION OF THE DRAWINGS

The photographs of *Kniphofia* 'Joker's Wild' demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
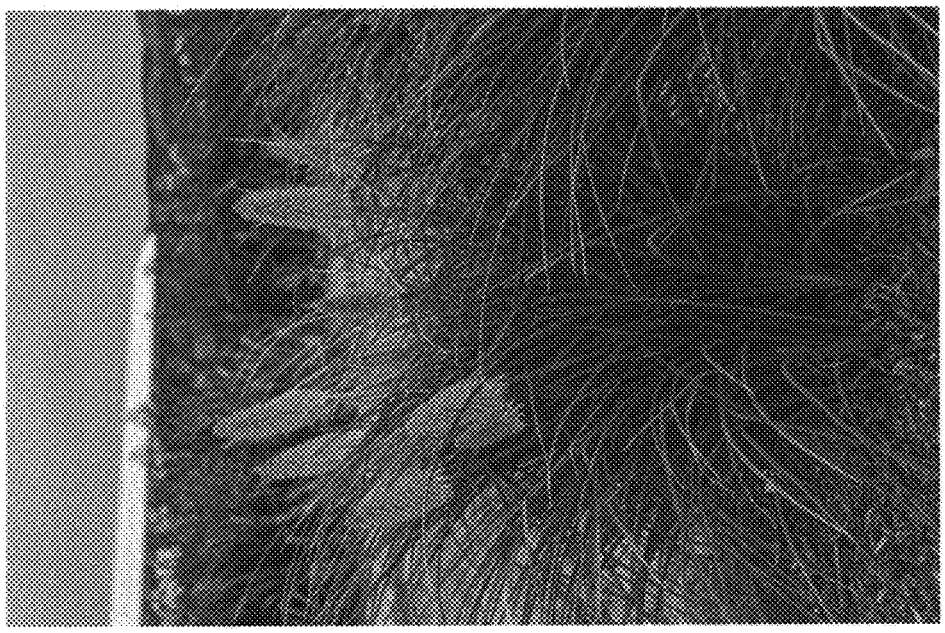
FIG. 1 shows the side-view habit of a five-year-old plant in midseason flowering.
Figure 2:
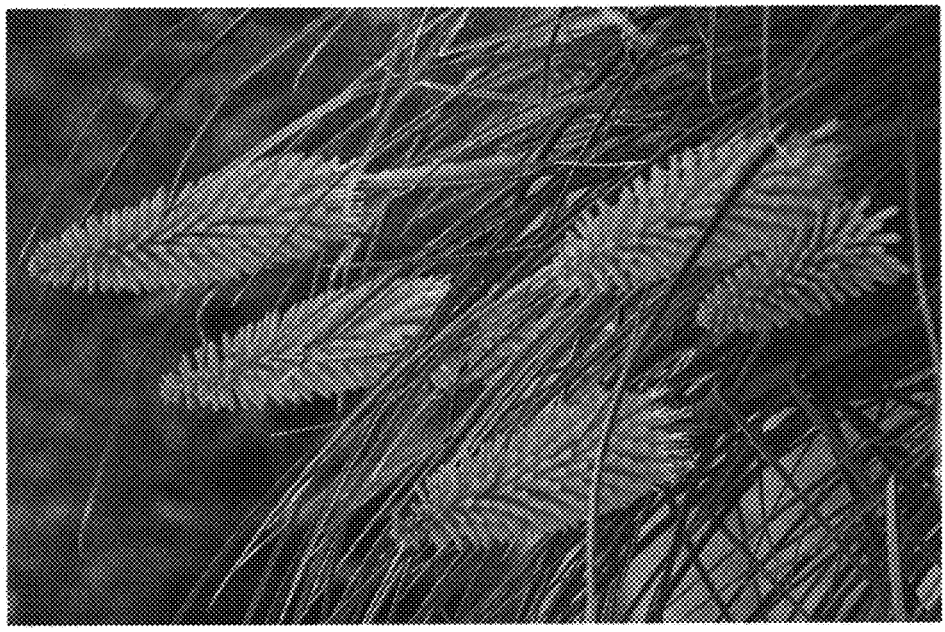
FIG. 2 shows a close-up of the flowers and buds.

The following descriptions and color references are based on the 2015 edition of The Royal Horticultural Society Colour Chart except where common dictionary terms are used. The new plant, *Kniphofia* 'Joker's Wild', has not been observed under all possible environments. The phenotype may vary slightly with different environmental conditions, such as temperature, light, fertility, moisture and maturity levels, but without any change in the genotype. The following observations and size descriptions are of two-year-old and five-year-old plants in a trial garden of a wholesale perennial nursery in Zeeland, Mich. under full sun with supplemental water and fertilizer as needed.

Botanical classification: *Kniphofia* hybrid;

Parentage: *Kniphofia* 'Alcazar' as the female or seed parent and as the male or pollen parent;

Propagation method: By garden division of the rhizome and shoot tip tissue culture;

Growth rate: Vigorous, flowering in 3.5 liter containers in about 10 to 12 weeks from a 25 mm plug liner in late winter to spring and from a one-year-old bare root plant to flowering in 6 to 8 weeks in a 4.0 liter container;

Rooting habit: Fibrous from base of rhizomes, lightly branching; color nearest RHS 158C;

Plant description: Dense, rhizomatous, acaulescent, perennial clump with long thin foliage to about 75.0 cm across and about 60.0 cm tall; flowering to about 70.0 cm tall; about 12 peduncles per plant;

Leaves: Linear; keeled at base, triangular in distal half; arranged up to 10 leaves per basal division; apex narrowly acute; base truncate, clasping; margin entire; no fragrance observed;

Leaf size: To about 65.0 cm long and 28.0 mm across at base, average about 58.0 cm long and 23.0 mm across at base;

Leaf color: Young base nearest RHS NN155C both abaxial and adaxial, distally between RHS 144A and RHS 138A both abaxial and adaxial; mature adaxial between RHS 137A and RHS 137B, abaxial nearest RHS 137B;

Leaf venation: Parallel; color same as leaf abaxial and adaxial;

Stem: Acaulescent; rhizome about 18.0 mm across at base;

Inflorescence: In spike-like raceme; cylindrical; about 150 flowers per stem; flowering portion to about 17.0 cm tall and about 5.0 cm across; lasting about three weeks; flower spacing less than 1.0 mm apart on raceme in distal region and about 2.5 cm in lowest flowers;

Peduncle: Cylindrical; glabrous; glaucous; stiff; upright; solid not fistulose; to about 70.0 cm long and 6.0 mm diameter; average 64.0 cm tall and 5.0 mm diameter; unbranched;

Peduncle color: Basal 5 cm nearest RHS 20D; distally nearest RHS 146B;

Buds one day prior to opening: Tubular with slightly swollen rounded apex and rounded base; glabrous; lustrous; about 18.0 mm long and about 2.5 mm diameter at base and 4.0 mm diameter at widest point near apex;

Bud attitude: Beginning outwardly and drooping as maturing toward anthesis;

Bud color: Abaxial one day prior to opening nearest RHS N30A distally and dorsally, ventrally and proximally nearest RHS 24B;

Flowers: Cylindrical forming tubular corolla; perfect; incomplete; actinomorphic; individually open and effective about three to four days;

Flower size: To about 31.0 mm long to tip of exserted anthers, fused in basal about 24.0 mm; face to about 8.0 mm tall and about 9.0 mm wide; corolla tube about 5.0 mm diameter near base and about 9.0 mm near throat; corolla tube to 19.0 mm long;

Flower attitude: Drooping;

Flower fragrance: None detected;

Flowering period: Individual racemes effective for about 3 weeks; beginning late summer for about three weeks in Michigan;

Tepals: Six, in two nearly identical sets of three; linear; both sets with acute apices and fused in basal 19.0 mm forming tube; margin entire; glabrous and lustrous abaxial and adaxial; about 22.0 mm long and about 2.5 mm across just above fusion point, about 3.0 mm long above fusion;

Tepal color (young and mature adaxial): Inner set corolla tube between RHS 28A and RHS 28B and apical face nearest RHS 24C, outer set nearest RHS N30C in apical face and corolla tube between RHS 28A and RHS 28B to base; (young and mature abaxial): inner set margin nearest RHS 29D, corolla tube nearest RHS N30D to base, outer set between N30C and RHS N30D and nearest RHS N30D to base;

Androecium: Six;

*Filaments*.—Six; exserted; straight; glabrous; lustrous; about 32.0 mm long and about 0.5 mm diameter; color nearest RHS 4D proximally, transitioning in distally nearest RHS 4B.

*Anther*.—Six; ellipsoidal; dorsifixed; longitudinal; about 2.0 mm long and 1.0 mm across and 1.0 mm thick; color ventrally nearest RHS 15B and dorsally nearest RHS 165A and center line nearest RHS N163C.

*Pollen*.—Abundant: color nearest RHS 12A.

Gynoecium: Single; about 31.0 mm long;

*Style*.—Cylindrical; straight; glabrous; lustrous; about 28.5 mm long and 0.5 mm diameter: color distally nearest RHS 9B and proximally nearest RHS 19D.

*Stigma*.—Flattened; about 0.5 mm across and tall; color nearest RHS 9B.

*Ovary*.—Superior; ellipsoidal; rounded apex, truncate base; about 3.0 mm long and 2.0 mm diameter; color nearest RHS 146D with slight blush of nearest RHS N163C.

Pedicel: Cylindrical; glabrous; slightly glaucous; stiff; arcuate downwardly with maturity; about 3.0 mm long and about 1.0 mm diameter;

Pedicel color: Nearest RHS N172B;

Bracts: Deltoid; at cauline nodes and subtending individual flowers; with acute apices and truncate base; to about 7.0 mm long and 5.0 mm across at base; decreasing distally; color between RHS 199D and RHS 164D;

Fruit: Tri-valved loculicidal capsule; globose to ellipsoidal; about 8.0 mm long and 7.0 mm across; glabrous; with rounded apex and rounded base; typically four to ten seeded; color as maturing nearest RHS 146A and upon maturity nearest RHS 199A;

Seed: Irregular with angular sides, acute apex and base; about 5.0 mm and 3.0 mm across; color nearest RHS 200A;

Disease and pest resistance: 'Joker's Wild' resistance beyond that of other *Kniphofia* has not been observed. The plant grows best with good drainage and is able to tolerate some heat when established. Hardiness at least from USDA zone 6 through 9 and 5b with protection.

I claim:

1. A new and distinct cultivar of *Kniphofia* plant named 'Joker's Wild' as herein described and illustrated.

* * * * *